United States Patent
Barton

(10) Patent No.: US 11,357,284 B2
(45) Date of Patent: Jun. 14, 2022

(54) ORTHOTIC DEVICE

(71) Applicant: KAYDIAR LTD., Swansea (GB)

(72) Inventor: David John Barton, Swansea (GB)

(73) Assignee: Kaydiar Ltd.

( * ) Notice: Subject to any disclaimer, the term of this patent is extended or adjusted under 35 U.S.C. 154(b) by 222 days.

(21) Appl. No.: 16/634,520

(22) PCT Filed: Jul. 27, 2018

(86) PCT No.: PCT/GB2018/052118
§ 371 (c)(1),
(2) Date: Jan. 27, 2020

(87) PCT Pub. No.: WO2019/021012
PCT Pub. Date: Jan. 31, 2019

(65) Prior Publication Data
US 2021/0100313 A1    Apr. 8, 2021

(30) Foreign Application Priority Data
Jul. 27, 2017 (GB) .................................... 1712079

(51) Int. Cl.
| A43B 7/1464 | (2022.01) |
| A43B 1/00 | (2006.01) |
| A43B 7/28 | (2006.01) |

(52) U.S. Cl.
CPC .......... A43B 7/1464 (2022.01); A43B 1/0009 (2013.01); A43B 7/28 (2013.01)

(58) Field of Classification Search
CPC ......... A43B 7/1465; A43B 7/28; A43B 7/148; A43B 1/0009; A61F 5/14
See application file for complete search history.

(56) References Cited

U.S. PATENT DOCUMENTS

| 2,288,665 A | * | 7/1942 | Anderson | A43B 7/1465 36/157 |
| 2,352,170 A | * | 6/1944 | Anderson | A43B 7/1465 36/157 |
| 4,598,484 A | * | 7/1986 | Ma | A43B 7/1465 36/141 |
| 5,096,188 A | * | 3/1992 | Shen | A61H 7/001 482/51 |

(Continued)

FOREIGN PATENT DOCUMENTS

| WO | 2004021817 A1 | 3/2004 |
| WO | 2006035469 A2 | 4/2006 |

OTHER PUBLICATIONS

Great Britain Search Report for Application No. GB1712079.1 dated Jan. 23, 2018.

(Continued)

*Primary Examiner* — Shaun R Hurley
*Assistant Examiner* — Bao-Thieu L Nguyen
(74) *Attorney, Agent, or Firm* — Tumey L.L.P.

(57) ABSTRACT

An orthotic device for footwear. In one embodiment the orthotic device comprises a substantially planar body having a resiliently deformable outer peripheral portion, a cell frame, and an inner array of detachably coupleable cells, wherein each cell comprises one or more protuberances and/or recesses which permit the cells to detachably couple with the cell frame.

17 Claims, 17 Drawing Sheets

(56) References Cited

U.S. PATENT DOCUMENTS

| | | | | |
|---|---|---|---|---|
| 5,186,703 | A * | 2/1993 | Huang | A61H 7/001 482/148 |
| 5,682,690 | A * | 11/1997 | Chang | A43B 7/00 36/11.5 |
| 7,013,588 | B2 * | 3/2006 | Chang | A43B 1/0054 36/141 |
| 9,516,917 | B2 * | 12/2016 | Hoffer | A43B 7/146 |
| 9,955,749 | B2 * | 5/2018 | Van Atta | A43B 7/146 |
| 10,258,110 | B2 * | 4/2019 | Sussmann | A43C 15/168 |
| 10,893,720 | B2 * | 1/2021 | Van Atta | A43B 13/122 |
| 10,939,723 | B2 * | 3/2021 | Walborn | A43B 7/141 |
| 2004/0045195 | A1 * | 3/2004 | Long | A43B 7/1465 36/88 |
| 2004/0230146 | A1 * | 11/2004 | Chang | A61H 7/001 601/134 |
| 2007/0084084 | A1 * | 4/2007 | Rich | A43B 17/026 36/44 |
| 2008/0010868 | A1 * | 1/2008 | Tsai | A43B 1/0081 36/141 |
| 2011/0064911 | A1 * | 3/2011 | Kuo | A43B 13/187 428/131 |
| 2011/0099845 | A1 * | 5/2011 | Miller | A43B 7/1465 36/91 |
| 2011/0289798 | A1 * | 12/2011 | Jung | A43B 7/1465 36/91 |
| 2012/0030969 | A1 * | 2/2012 | Lim | A43B 17/00 36/141 |
| 2012/0272545 | A1 * | 11/2012 | Chenut | A43B 17/02 36/43 |
| 2013/0118032 | A1 * | 5/2013 | Raji | A43B 3/128 36/100 |
| 2013/0318818 | A1 * | 12/2013 | Gardiner | A43B 13/38 36/43 |
| 2014/0034068 | A1 * | 2/2014 | Picar | A61F 5/0195 128/888 |
| 2015/0075030 | A1 * | 3/2015 | Walborn | A43B 13/386 36/44 |
| 2015/0196082 | A1 * | 7/2015 | Van Atta | A43B 13/125 36/103 |
| 2016/0007671 | A1 * | 1/2016 | Prust | A47C 27/007 2/411 |
| 2016/0235158 | A1 | 8/2016 | Desjardins et al. | |
| 2017/0055629 | A1 * | 3/2017 | Schickling | A43B 13/026 |
| 2017/0071289 | A1 * | 3/2017 | Auyang | A43B 13/188 |
| 2017/0332727 | A1 * | 11/2017 | Beck | A43B 13/125 |
| 2017/0348181 | A1 * | 12/2017 | Perriard | A43B 13/189 |
| 2018/0242683 | A1 * | 8/2018 | Van Atta | A43C 15/14 |
| 2018/0317591 | A1 * | 11/2018 | Hollinger | A43B 7/1445 |
| 2019/0297995 | A1 * | 10/2019 | Loveder | A43B 13/12 |
| 2020/0107612 | A1 * | 4/2020 | Schickling | A43B 7/142 |
| 2020/0170335 | A1 * | 6/2020 | Horvath | A43B 1/0009 |
| 2021/0106095 | A1 * | 4/2021 | Van Atta | A43C 15/14 |

OTHER PUBLICATIONS

International Search Report and Written Opinion for Application No. PCT/GB2018/052118 dated Oct. 17, 2018.
Great Britain Search Report for Application No. GB1812269.7 dated Feb. 6, 2019.

* cited by examiner

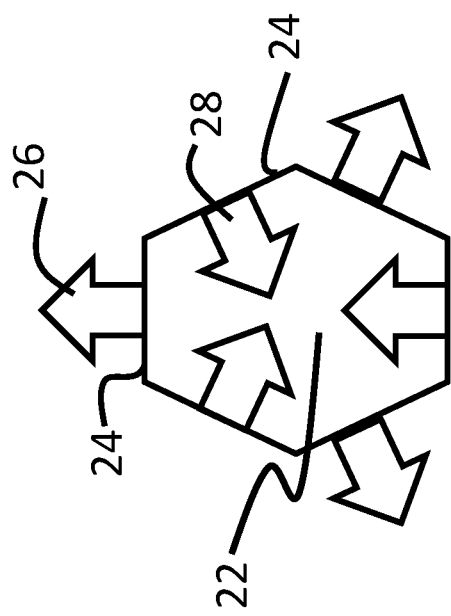
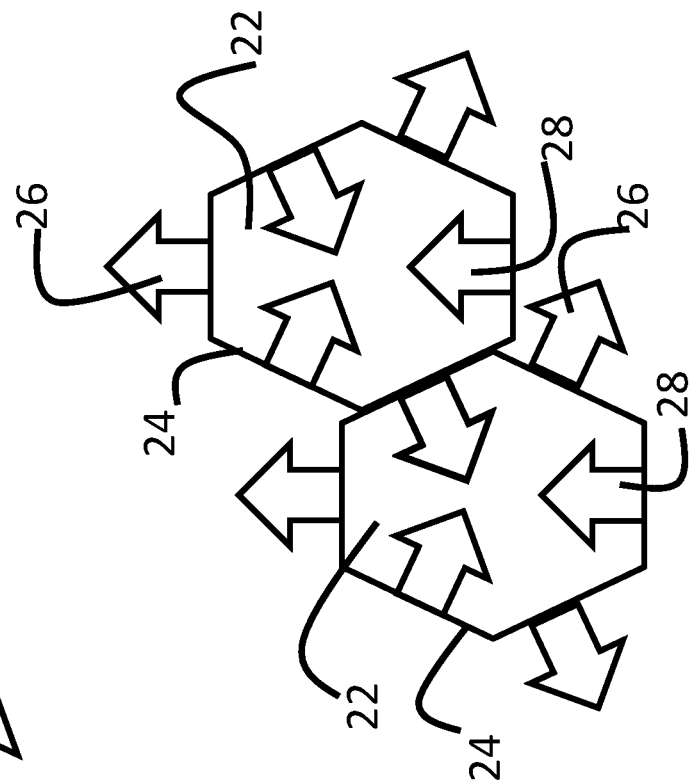
Figure 3A
Figure 3B

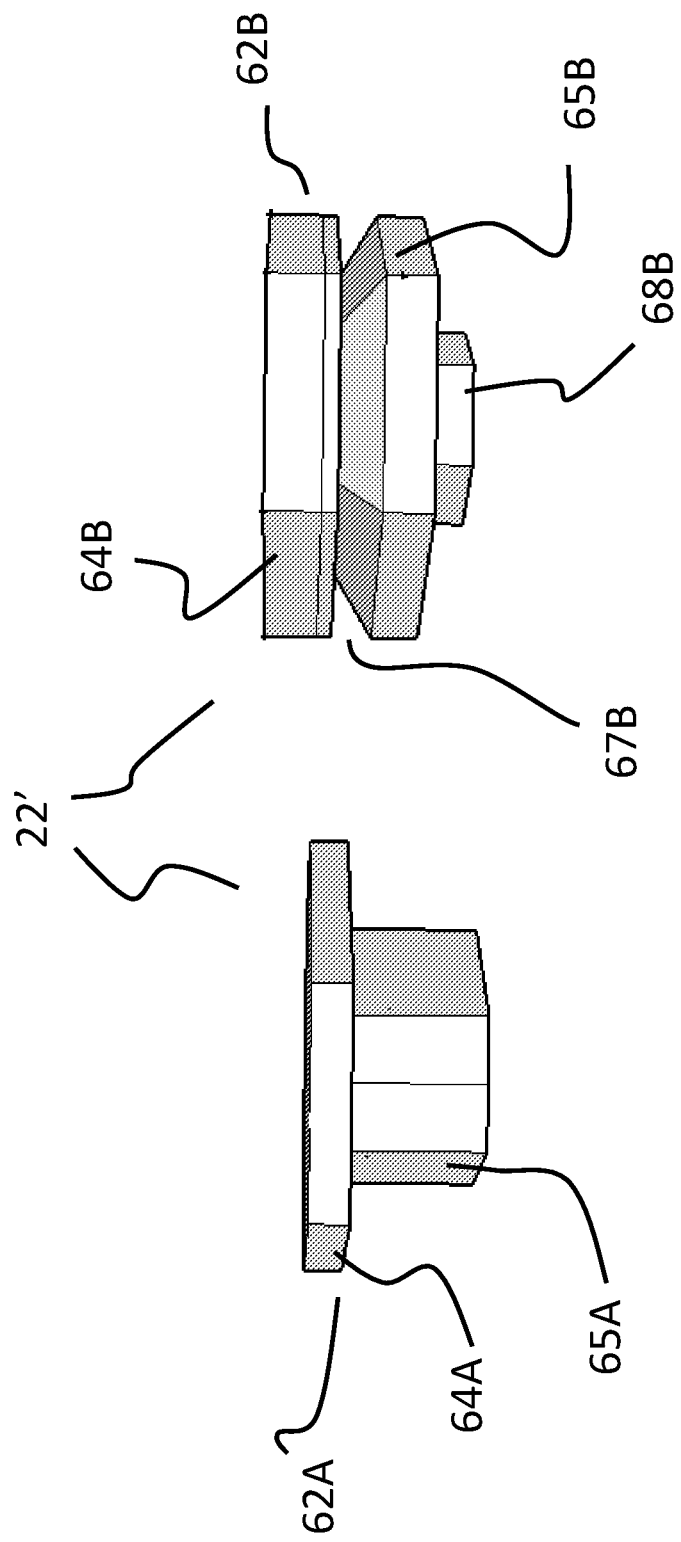

ORTHOTIC DEVICE

The present invention relates to a medical orthotic device composed of individual coupleable cells to provide a customisable, adhesive free insole that can offload high-pressure areas of the foot.

Foot orthoses or shoe inserts are well known and used for a number of purposes including daily wear comfort, foot and joint pain relief from arthritis, overuse injuries, and other causes such as orthopaedic correction, smell reduction and athletic performance. Foot orthoses comprise a custom made insert or footbed fitted into a shoe, commonly referred to as "orthotics", these orthoses provide support for the foot by redistributing ground reaction forces as well as realigning foot joints while standing, walking or running.

The primary purpose of orthoses is to remove or reduce pressure, typically referred to as offloading, from problematic plantar foot lesions that have resulted from abnormal pressure, in particular neuropathic ulcerations (open sores that are difficult to heal) associated with diabetes: a disease in which the body's ability to produce or respond to the hormone insulin is impaired, resulting in elevated levels of glucose in the blood, otherwise known as hyperglycaemia. Chronic hyperglycaemia is known to cause irreversibly damage to peripheral nerves resulting in decreased or abnormal sensation (neuropathy). Due to this lack of sensation in the feet, diabetic patients are prone to ulceration as they cannot feel any stimulus to trauma or abnormally high pressure points that are involved in ulcer formation.

In addition to diabetic ulceration, orthoses may be used to offload symptomatic lesions that may not be associated with diabetes, such as painful corns, callus and verrucas.

The overall aims of orthoses are as follows:
1. To optimise the healing of active diabetic neuropathic ulcers by directly offloading these lesions, thus removing pressure and preventing further breakdown;
2. To prevent future or recurrent ulceration by offloading high pressure points;
3. To manage painful plantar lesions (such as neurovascular corns, verrucas, and hyperkeratosis);
4. Improve dynamic foot function; and,
5. Provide a cost-effective treatment option for diabetic ulcers for medical professionals.

There currently exist orthotic devices aimed at offloading for diabetic ulcers. For example U.S. Pat. No. 8,201,346 discloses a medical shoe system having a multi-layered foam orthoses which consists of pegs within its inner body which enables offload in a specific area of the foot. However, there are multiple limitations associated with orthoses of this type:
  The orthoses suffer significant compression over a short period of time;
  Are formed from open cell material which is not hygienic and can harbour bacteria;
  Are not resistant to shear forces from users;
  Requires use of industrial carcinogenic glue to combine the foam layers;
  Only fits in custom surgical shoes, therefore is not able to fit into conventional footwear; and,
  Suffer from a short lifespan.

The present invention overcomes at least some of the limitations of current orthoses. The detachably coupleable cell design of the current device allows offload on any area of the foot at multiple locations, the size and shape of the orthoses can also be adjusted to fit the patient's foot type or shoe. Due to full customization of the orthotic device, it is easier to achieve patient compliance because of its ability to roughly adapt to the patients shoe without causing discomfort. Specialized cells can be used to create a periphery around the orthotic device so that a clinician can assemble a larger or smaller circumference around the orthoses in order to fit patient's shoes.

All of the features of the invention benefit the clinician and patient, and comprise at least the following advantages:
  Full customisation of tissue/wound offloading and can be applied into most closed footwear and surgical boots.
  Ease of use to assemble and take apart.
  Ready to give to patients immediately (i.e. same day as the appointment) with instant relieving effects.
  No industrial (carcinogenic) glue is needed to assemble the device and grinders are not required to smooth edges as they are already smooth and comfortable via use of 3-D modelling/printing software.
  Appropriate for domiciliary work and for clinicians whom are not fortunate enough to have an orthotics lab on site.
  Cuts time due to ease of cell joint assembly and thus decreases long term expenditure (industrial glues are a consistent expenditure in the long run, and loud expensive grinders). Additionally, the orthoses have a long life span, reducing raw material costs for making orthotics.

In accordance with the present invention as there is provided an orthotic device for footwear, comprising a substantially planar body having a resiliently deformable outer peripheral portion, a cell frame and an inner array of detachably coupleable cells, each cell comprising coupling means which permit the cells to detachably couple with the cell frame.

In an embodiment the cell coupling means may permit the cells to detachably couple with each other. Furthermore the cell coupling means may permit the cells to detachably couple with the outer peripheral portion In an embodiment, the outer peripheral portion comprises a continuous portion which extends around a periphery of the body. In an alternative embodiment, the outer peripheral portion comprises a plurality of peripheral segments each comprising coupling means, which permit the peripheral segments to detachably couple together.

In an embodiment, the cells comprise a substantially cube like or hexagonal prism shape. The cells may further comprise a plurality of cell faces and the number of cell faces may be varied to create different cell shapes which may be more advantageous under certain conditions.

The coupling means may comprise one or more protuberances and/or recesses disposed on the cells faces. The protuberances preferably extend outwardly of the cell, away from the respective cell face, whereas the recesses preferably extend inwardly of the cell, from the respective cell face. The amount of and type of coupling means may be varied to be more advantageous in certain conditions. For example, some cells may be classified as male or female, having only protuberances or recesses respectively.

In an embodiment, the device further comprises a longitudinal axis which extends between a front and rear of the footwear, and a lateral axis which extends between a left and right side of the footwear, substantially transverse to the longitudinal axis wherein the cells are orientated such that an interface between neighbouring cells extends non-parallel with the longitudinal axis and lateral axis. This misalignment of the cell interfaces with the shoe and principally the longitudinal axis of the shoe provides for a more resilient coupling between the cells and if present the segments of the body. The user's foot would typically move within the shoe, along the longitudinal axis during use and thus create shear forces between cells and if present, the segments of the body. This force is reduced by orientating the interface between cells away from the longitudinal axis and thus minimises any undesired uncoupling of the cells of the body.

The orthotic device may be formed substantially of silicone or a closed cell material having a translucent or transparent property. There are multiple advantages of a silicone based material including a balance between shock absorption and firmness as well as mild bacterial static properties. Having closed cell material makes it virtually impossible for bacteria to thrive and remain dormant in the device. The immediate benefits of translucent or transparent materials help with setting up the device and monitoring progress.

In an embodiment the detachably coupleable cells each comprise a first cell portion and a second cell portion which are detachably coupleable. Furthermore the first portion and second portion may comprise a male or female connector.

In an embodiment the orthotic device may further comprise a cell frame. Furthermore the cell frame may comprise a resiliently deformable mesh defining a plurality of apertures.

In an embodiment the detachably coupled cell comprises a base and a cap, wherein the cell coupling means comprise a channel formed between the base and the cap. Furthermore the cell frame may be located in the channel of the cell when the cell is coupled to the frame.

In an embodiment the orthotic device may further comprise one or more cell modules, wherein a cell module comprises a body and one or more detachably coupleable cells.

The invention may be performed in various ways and embodiments thereof will now be described, by way of example only, reference being made to the accompanying drawings, in which:

FIGS. 3A and 3B are plan views of an alternative embodiment of the detachably coupleable cells in an uncoupled and coupled configuration respectively;

FIGS. 6A and 6B are a cross section of an alternative embodiment of a detachably coupleable cell showing first male portion and second female portion respectively;

Figure 1:
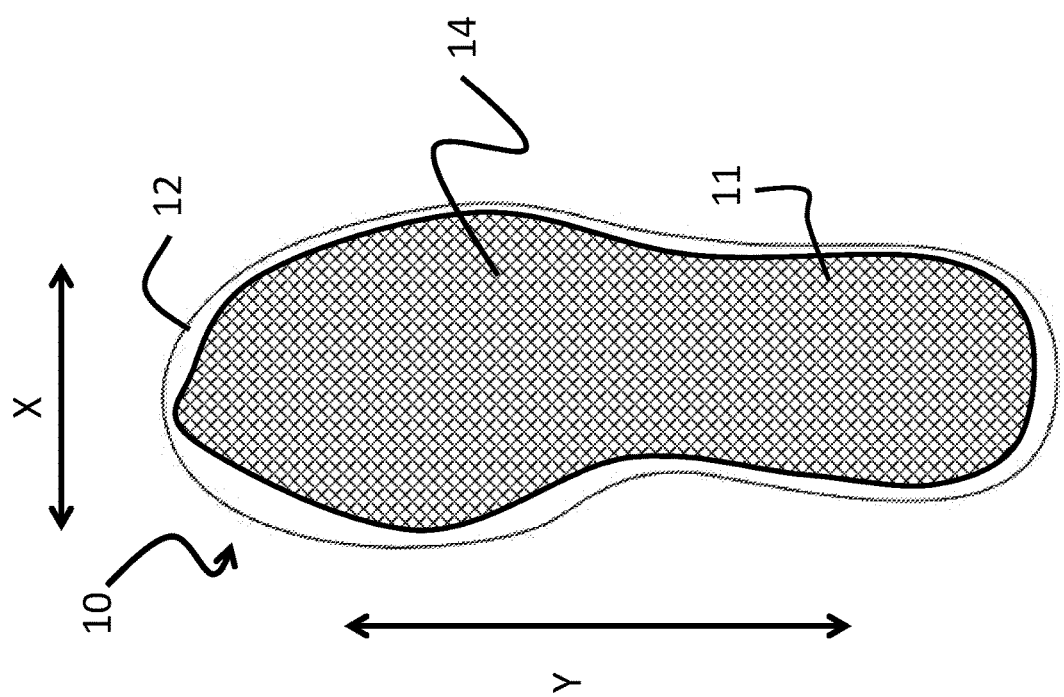
FIG. 1 is a plan view of an orthotic device according to an embodiment of the present invention.

Referring to FIG. 1 of the drawings, there is illustrated a plan view of an orthotic device according to any embodiment of the present invention. The device 10 comprises a resiliently deformable, substantially planar body 11 formed of silicone or a closed cell material, comprising an outer peripheral portion 12 and an inner array 14 of detachably coupleable cells 22 (as illustrated in FIGS. 2-4 of the drawings). It will be appreciated from FIG. 1 that although the overall shape of the device is arranged to conform to an interior shape of a shoe (not shown); the shape may be varied to accommodate many different requirements. For example, the device may also be used for other healthcare applications including patients who are confined to wheelchairs and who require pressure reduction or offload of their lower back and buttocks, and people whom are bed bound and susceptible to bed sores. The resiliently deformable outer periphery allows for some degree of deformation in response to pressure from a foot or shoe wall, such that it will fit securely into multiple shapes of shoe. The outer peripheral portion may comprise a single continuous portion or a plurality of detachably coupleable peripheral segments.

Figure 2A:
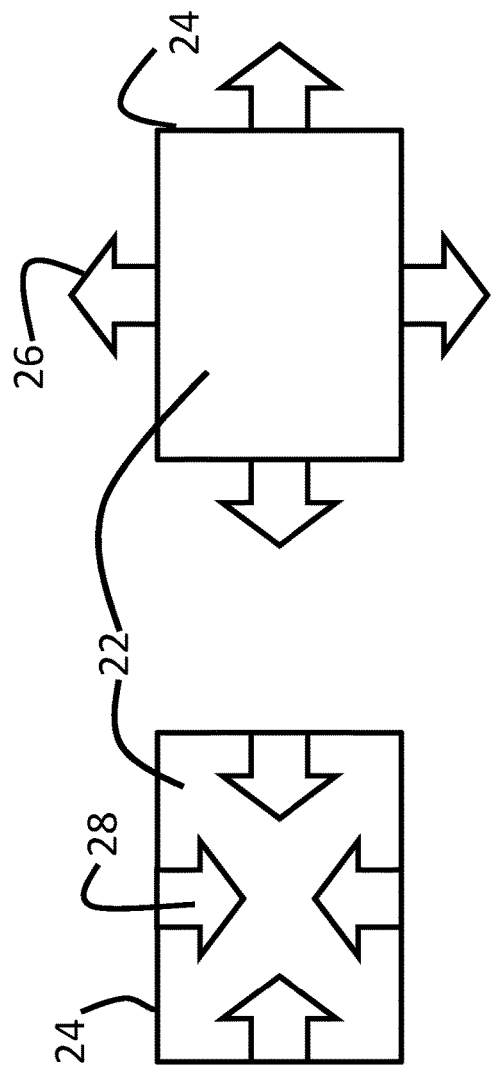
FIGS. 2A and 2B are plan views of an embodiment of the detachably coupleable cells in an uncoupled and coupled configuration respectively.

Referring now to FIG. 2A there is shown an embodiment of two detachably coupleable cells 22 of the array, arranged in a detached configuration. The cells comprise a plurality of side faces 24 which extend between an upper and lower face, substantially perpendicular thereto. The upper and lower face of each cell collectively form an upper and lower surface of the body 11, with the upper surface being arranged to form a contact with a user's foot and the lower surface contacting an inner base of the shoe (not shown). FIG. 2A illustrates a female cell having a plurality of recesses 28 only, disposed in the side faces 24, and a male cell having a plurality of protuberances 26 only, disposed on the side faces 24. The recesses extend into the cell 22, away from the respective cell face, whereas the protuberances extend outwardly of the cell 22 away from the respective cell face.

Figure 2B:
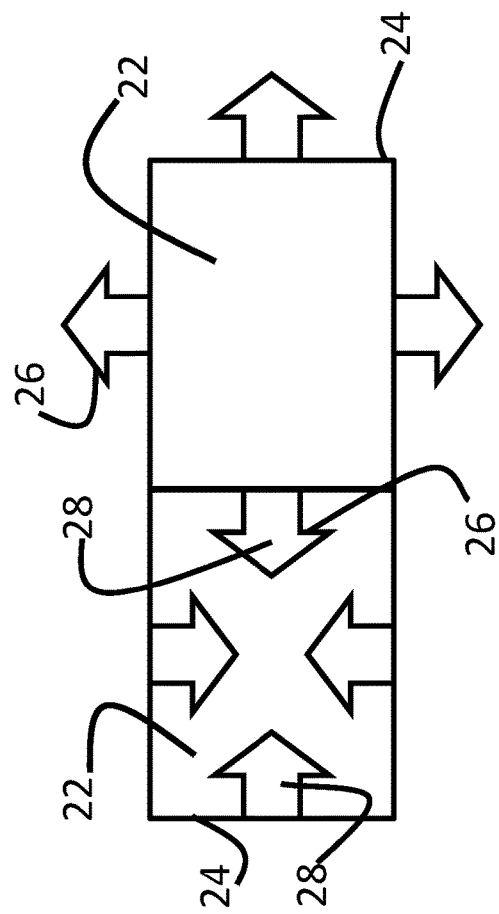

FIG. 2B illustrates the cells 22 in a coupled configuration in which a protuberance 26 of the male cell is inserted within a recess 28 of the female cell forming a coupling there between. It will be appreciated that the coupling means may be one of many kinds of detachably coupleable formations known to the person skilled in the art, such as friction locking or rotational engagements etc. The protuberances 26 are shaped to correspond with a shape of the recesses 28 and the skilled person will recognise that alternative shapes could be used.

The cell faces 24 of the cells 22 disclosed in FIG. 2 comprise a quadrilateral shape, such as square or rectangle, and the resulting shape of the cells may comprise a cuboid or hexagonal prism (see FIG. 3) for example, although it will be appreciated that there are many other shapes that could be formed by including cells having different numbers of side faces 24.

The cells faces 24 may comprise a single recess 28 or protuberance 26 disposed substantially centrally thereof, or one or more of the side faces 24 may comprise a plurality of recesses 28 and/or protuberances 26 distributed across the respective face. In this case, the recesses/protuberances 28, 26 must be located at corresponding locations to the protuberances/recesses 28, 26 on cell faces of adjacent cells to permit a detachably coupling there between.

In a further embodiment and particularly for the peripheral portion 12 or segments 42 (see FIG. 5) of the peripheral portion 12, one side face is preferably free from any coupling means. This side face is arranged to form an outermost peripheral edge of the body 11 and thus the orthotic device and as such, the outer side face is not arranged to couple with any further cells.

It will be appreciated that there is a depth dimension (Z) associated with the cells 22 that is not shown in the Figures. Cells 22 may be chosen having a variety of depth dimensions to suit various needs of the user. For example, dealing with large ulcers and larger body parts the device 10 may require the use of thicker cells with a larger cross-sectional area, whereas smaller ulcers may require smaller cells to provide a more refined removal of cells to create a more refined void in the body. On average, the cell dimensions are sized such that each cell occupies approximately 1 cm$^3$. The coupling means may also vary in dependence of cell size, however, it is envisaged that the average size for a protuberance 26 for example will be in the range of 2-5 mm.

The cells 22 may be produced using modern 3-D printing techniques, creating cells 22 with an accuracy of 100 microns. Being able to produce very small intricate designs allows for more complex innovative design to be produced. The outer periphery 12 and inner array 14 of cells 22 of the body 11 may be made from the same or different material. Silicone has a high temperature resistance and can therefore be used for long term applications. Silicone impregnated with platinum can improve the hygiene and longevity of the device, thus the device 10 becomes extremely cost effective.

Referring now to FIGS. 3A and 3B there is shown an alternative embodiment of the detachably coupleable cells 22, both individually and when coupled. In this embodiment the cells 22 are hexagonally shaped and each cell 22 comprises both protrusions 26 and recesses 28. The cells 22 illustrated in FIGS. 2 and 3 are orientated such that an interface between neighbouring cells 22 extends non-parallel with a longitudinal axis and a lateral axis of the shoe (not shown) in which the orthotic device 10 is to be inserted. This non-parallel orientation improves the resistance of the device 10 to shearing forces created by movements of the user's foot within the shoe and thus minimises separation of cells 22 within the array.

Figure 4B:
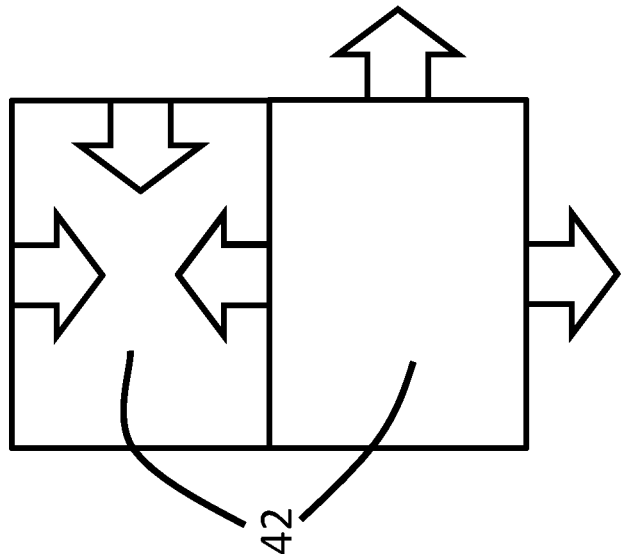
FIGS. 4A and 4B are plan views of an embodiment of the outer periphery comprising detachably coupleable segments in an uncoupled and coupled configuration respectively.
Figure 4A:
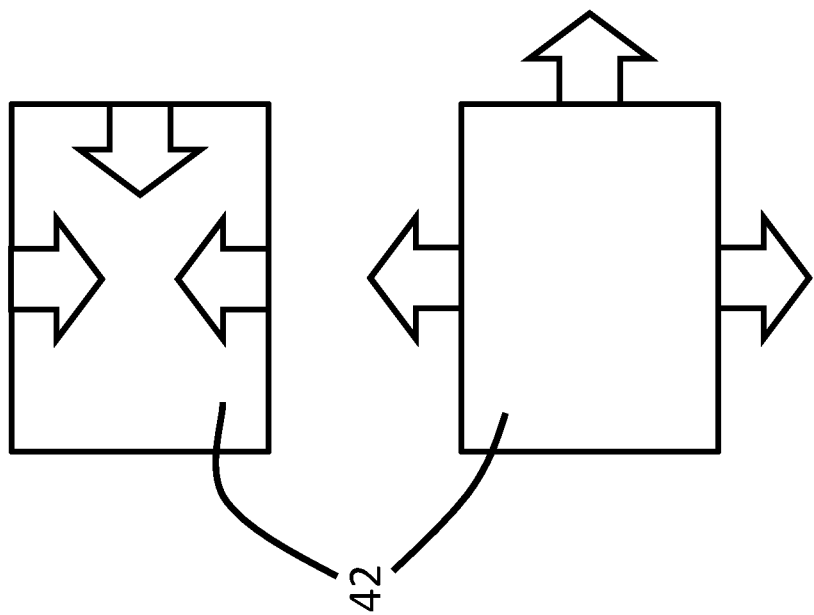

Referring now to FIGS. 4A and 4B there is illustrated an embodiment of the resiliently deformable outer periphery of the body 11 which is composed of detachably coupleable segments 42. The detachably coupleable segments are substantially similar to the cells and comprise similar coupling means. However, one side face of the segment, namely the side face forming the outer side of the body 11, does not comprise any coupling means and is arranged to form the outermost periphery of the body 11.

Figure 5:
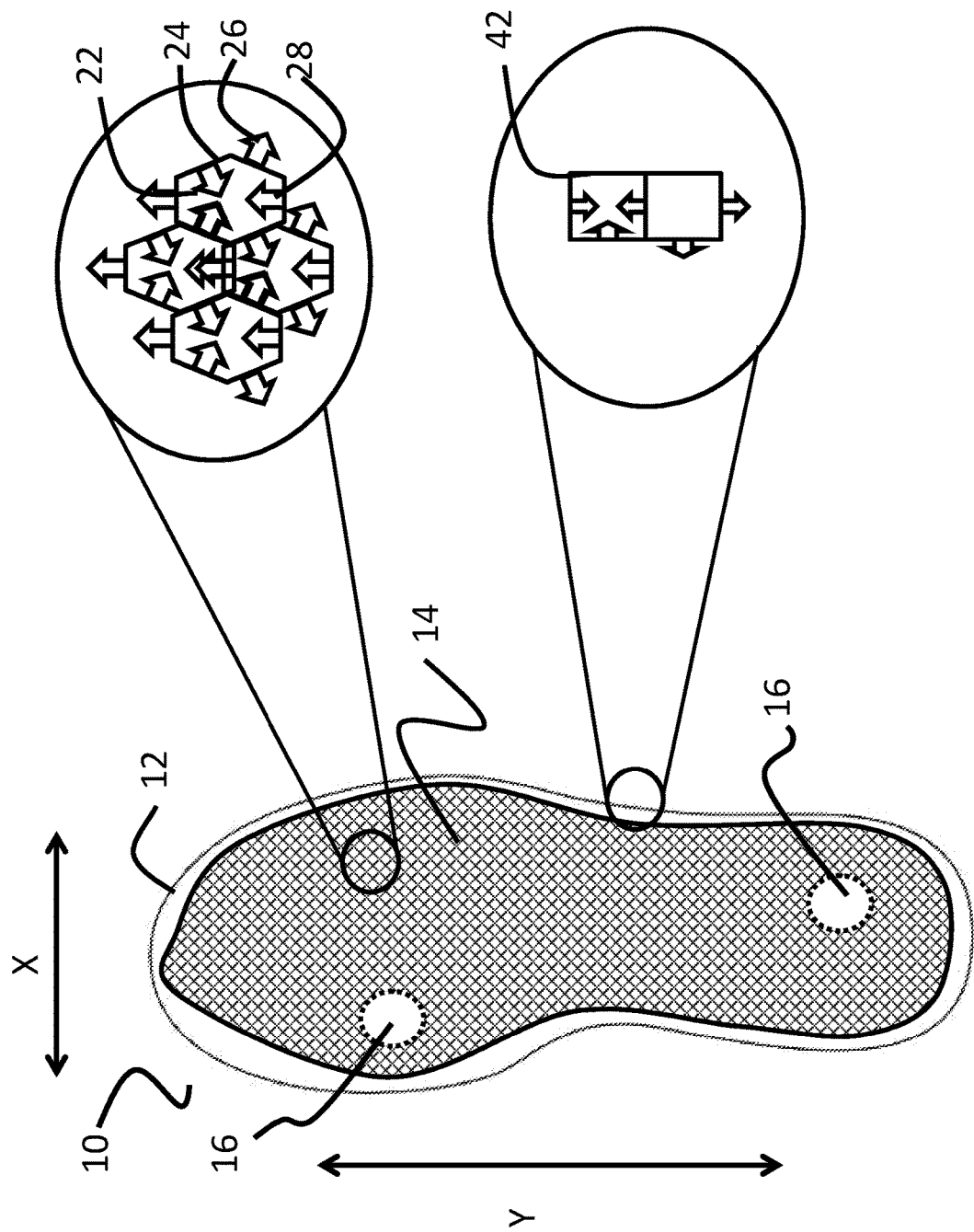
FIG. 5 is a plan view of an alternative embodiment of the present invention.

FIG. 5 shows a representation of an embodiment of the invention wherein some cells 22 have been removed creating voids 16 in the body 11 to reduce pressure at these contact points with the user's foot (not shown). During use, a clinician for example would place the complete orthotic device 10 adjacent the underside of a patient's foot (not shown) and the translucent/transparent property of the body 11 enables the clinician to associate the trauma locations on the patient's foot with the corresponding location on the body 11 of the device 10. This enables the clinician to remove those cells 22 corresponding to the location of the trauma to create the voids 16 in the body 11 at these locations which require offloading. Referring to FIG. 5 of the drawings, there are also shown magnified views of areas of the device 10 showing the inner array of detachably coupleable cells and the detachably coupleable segments comprising the resiliently deformable outer periphery. As the device is hygienic and the cells 22 are capable of being reattached to fill the voids 16, it is envisaged that, this device 10 can be subsequently re-configured for another user.

FIGS. 6 to 17 of the drawings illustrate further features of an orthotic device according to a further embodiment of the present invention. The advantages of the invention as described in the previous embodiments are envisaged to be further enhanced by the following embodiments.

Referring now to FIGS. 6A and 6B there is shown an alternative embodiment of a detachably coupleable cell 22, namely alternative cell 22' wherein the cell 22' comprises a first portion 62A and a second portion 62B. The portions are detachably coupleable (or separably joinable) to create a single cell, for example in a manner similar to a snap fastener. FIG. 6A illustrates a first portion as a male type connector shown comprising a stud base 64A and a post 65A which is a sleeve containing a protuberance 66 (not shown). FIG. 6B illustrates a second portion as a female type connector shown comprising a cap 64B and a socket 65B. There is a gap 67B formed between the cap and socket, which as the cell is formed of a resiliently deformable material can allow compression under load, yet maintain a connection between the first and second portions. There is a sleeve 68B which defines the circumference of a recess 68 (not shown).

In a preferable embodiment, when combined, the male and female portions form detachably coupleable cell 22' comprising a depth of approximately 6 mm. The individual male and female portions are approximately 4.3 mm in depth however it will be appreciated that the dimensions of the cells may be modified to suit individual circumstances. It will be appreciated that either the first portion or second portion could be a male or female portion.

Figures 7A, 7B:
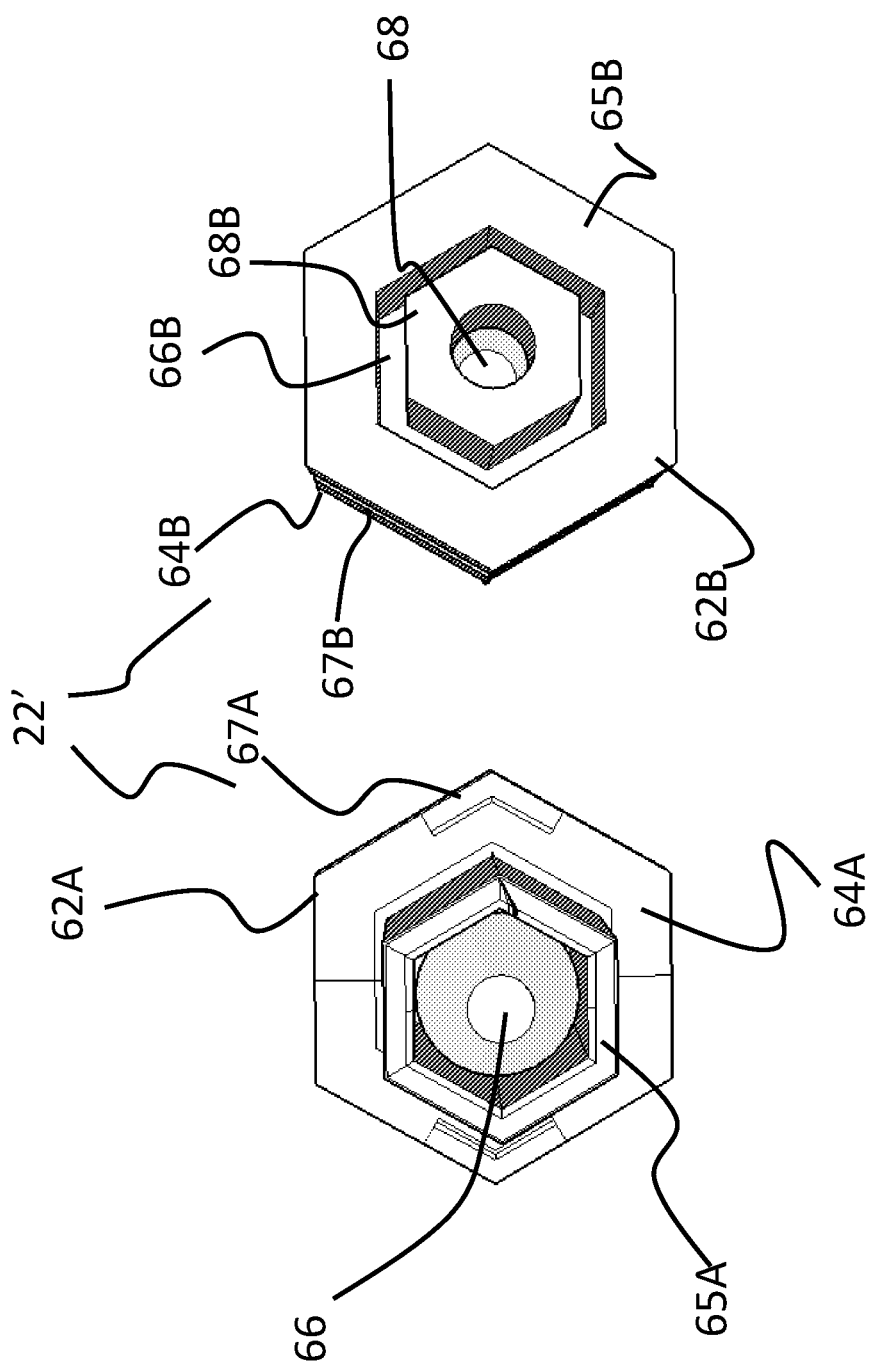
FIGS. 7A and 7B are top down views of the detachably coupleable cell shown in FIGS. 6A and 6B respectively.

Referring now to FIGS. 7A and 7B there is shown the alternative embodiment of a detachably coupleable cell as seen in FIGS. 6A and 6B, from the underside thereof. FIG. 7A illustrates a first portion 62A as a male type connector shown comprising a stud base 64A and a post 65A which is a sleeve is containing the protuberance 66. Further shown is abutment feature 67A, which contacts socket 65B when the portions are joined and acts to reduce the surface contact and prevent adhesion. FIG. 7B illustrates a second portion as a female type connector shown comprising a cap 64B and a socket 65B, there is a gap 67B formed between the cap and socket. There is a sleeve 68B which defines the circumference of a recess 68. Further shown is a channel 66B which receives the post 65A when the portions are joined.

The first cell portion 62A and second cell portion 62B are illustrated as a substantially hexagonal prism shape when combined in a cell 22', although it will be appreciated that there are many other shapes that could be formed.

Figure 8:
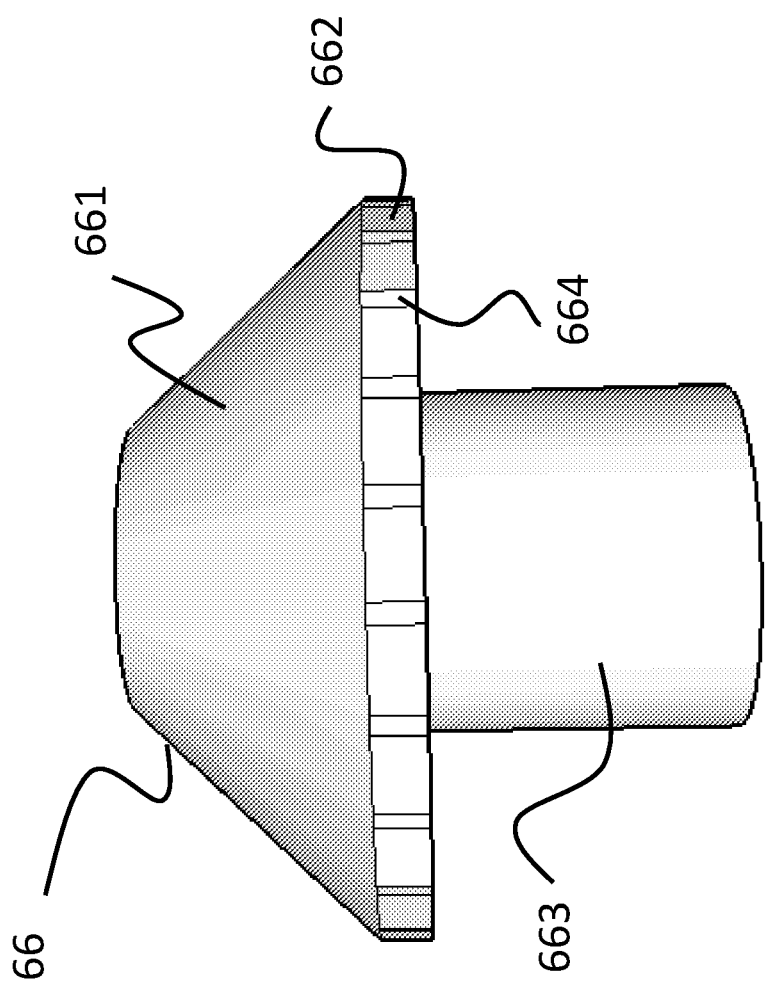
FIG. 8 is a protuberance of the detachably coupleable cell shown in FIG. 6A.

FIG. 8 shows a representation of an embodiment of the protuberance 66 as may be used in the embodiment of the detachably coupleable cell 22' as seen in FIGS. 6A and 7A. The protuberance illustrated comprises a frusta-conical head 661, a cylindrical shaft 663 and a band 662 around the periphery of a base of the head. The illustrated embodiment of the protuberance improves the connection between the first and second portions. The frusta-conical head 661 reduces the frictional force required to couple/join the portions, compared with a greater force required to detach/separate the portions. The band 662 may be provided with channels 664 which may further improve the coupling/ joining and detaching/separation mechanisms, by reducing the required force to overcome friction between the protuberance and recess. It will be appreciated that shapes and dimensions of the protuberance may be modified to suit individual circumstances. It will be appreciated that the design of the recess 68 will be the appropriate reverse image to receive the protuberance.

Figure 9:
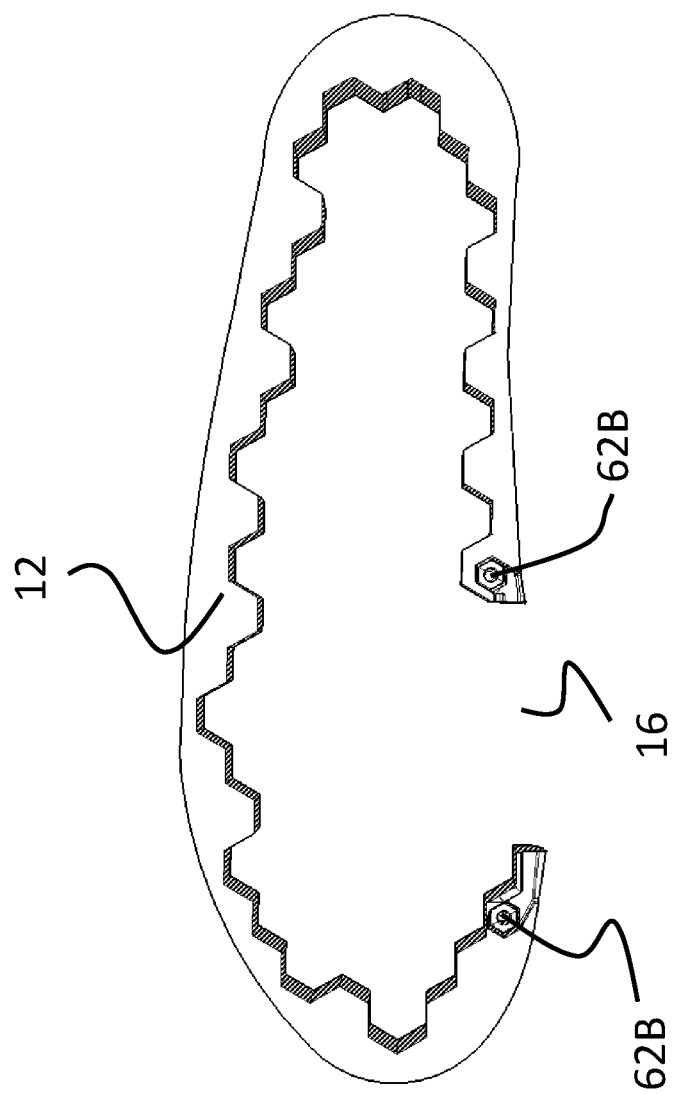
FIG. 9 is a plan view of an embodiment of the outer periphery.

FIG. 9 shows a representation of an embodiment of the resiliently deformable outer periphery 12 which may be composed of detachably coupleable segments 42/42'. In the embodiment shown, the periphery has a void 16 where the patients $1^{st}$ toe would be located. Adjacent the void 16 on each side and formed on the periphery 12 can be seen second portions 62B of detachably coupleable cells 22, this will allow segments 42/42' to be coupled to the periphery.

Figure 10:
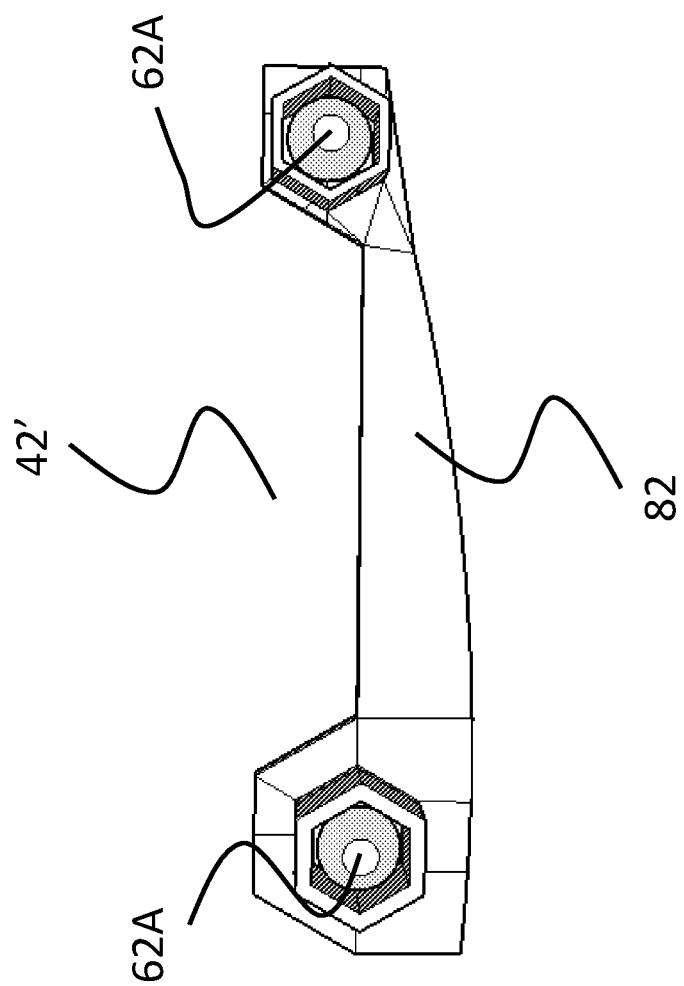
FIG. 10 is a top down view of a detachably coupleable cell arrangement which cooperates with the outer periphery as shown in FIG. 9.

Referring now to FIG. 10 there is illustrated an alternative embodiment of a segment 42, namely a modified segment 42'. The modified segment 42' comprises a resiliently deformable bridge 82 suitable for completing the outer periphery shown in FIG. 9. The bridge 82 comprises a first portion 62A of the detachably coupleable cells 22 disposed at each end thereof, which are arranged to align with the second portions 62B as shown in FIG. 9.

Figure 11:
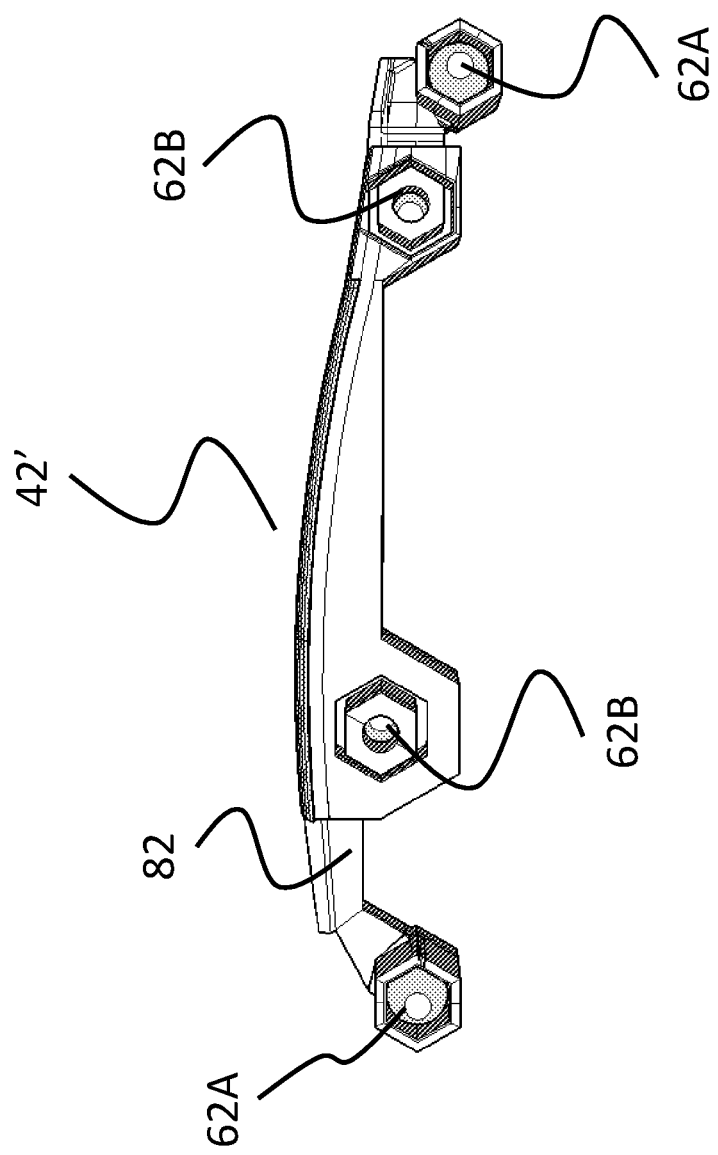
FIG. 11 is a top down view of a detachably coupleable cell arrangement which cooperates with the outer periphery as shown in FIG. 9.

Referring now to FIG. 11 there is illustrated an alternative embodiment of a modified segment 42'; in this embodiment, the bridge 82 comprises two first portions 62A of detachably coupleable cells 22', one disposed at each of the bridge 82, which are arranged to align with the second portions 62B as shown in FIG. 9. Furthermore, the modified segment 42' further comprises two second portions 62B of detachably coupleable cells 22', one disposed towards each end of the bridge 82, which can be used to attach further bridges 82 or other offloading modules (FIG. 13) or cells. It will be appreciated that the bridges 82 can be formed with many types of musculoskeletal (MSK) components for assembly into orthoses to aid complex MSK pathologies.

Figure 12:
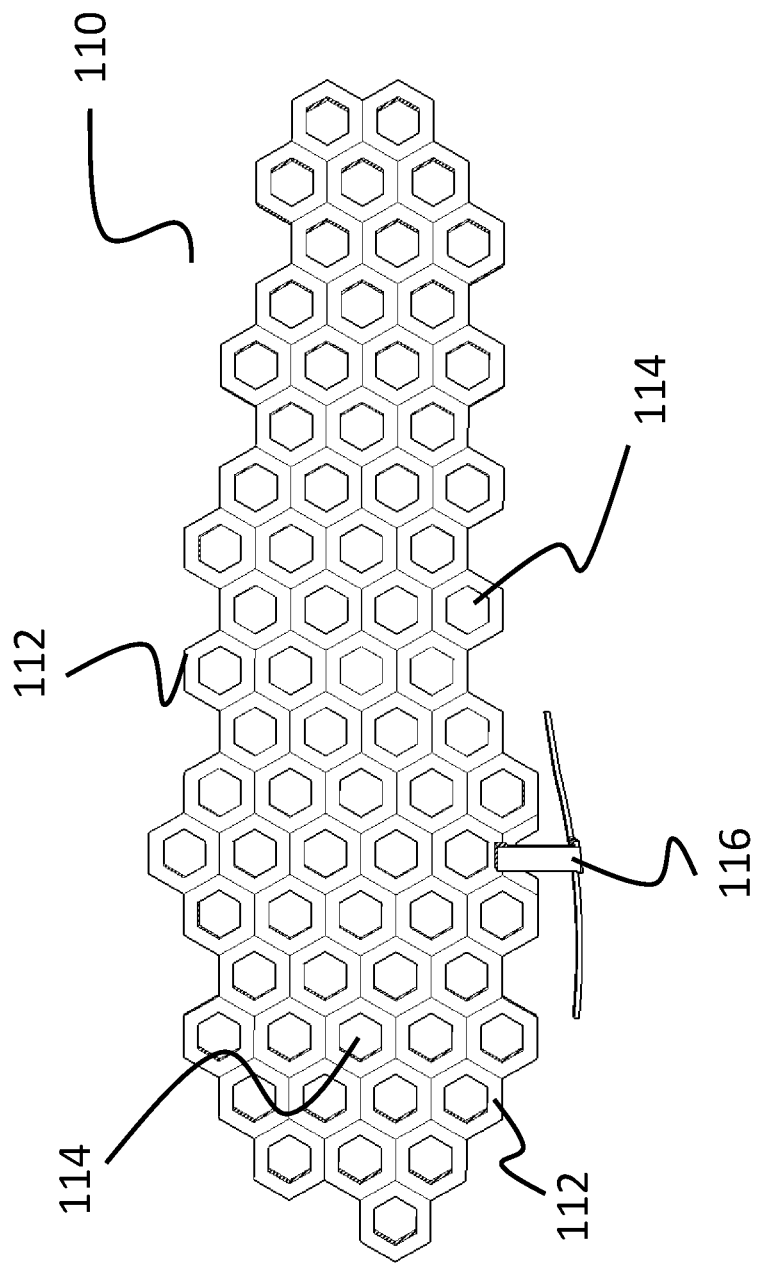
FIG. 12 is a plan view of a cell frame.

FIG. 12 shows a cell frame 110 for use in an embodiment of the present invention. The cell frame comprises a resiliently deformable mesh 112, the mesh defining a plurality of apertures 114. The mesh 112 can be placed within an outer periphery 12, providing additional support and structure to the orthotic device 10. The apertures 114 provide a template for allowing detachably coupleable cells 22' to be located. The frame 110 may be provided with an additional attachment structure 116 which can enable the frame to be attached to the outer periphery 12, the attachment structure 116 may be placed at any position on the frame and more than one may be used. Furthermore, in the embodiment where the detachable cells comprise a first portion 62A and second portion 62B, the first and second portions are arranged to detachably couple together either side of the mesh 112, such that the mesh 112 is disposed between the coupled portions 62A, 62B. In use the cell frame 110 may be located within or formed integrally with an outer periphery 12. The cell frame can also be produced with an array of cells in situ. Where the cells 22' are comprised of first and second portions, the portions may be separated by a user and removed from the mesh 112 form a void 16. It will be appreciated that the sleeve 65A surrounding the protuberance 66 of the first portion 62A extends through the cell frame apertures 114 to engage with the recess 68 of the second portion 62B, the stud 64A and opposing socket 65B are arranged to abut the frame 110. The frame 110 provides additional structural integrity to the device 10, for example allowing it to be inserted easier into a user's shoe and wherein the cells are comprised of a first and second portion it will have greater resilience to shear stresses.

Figure 13:
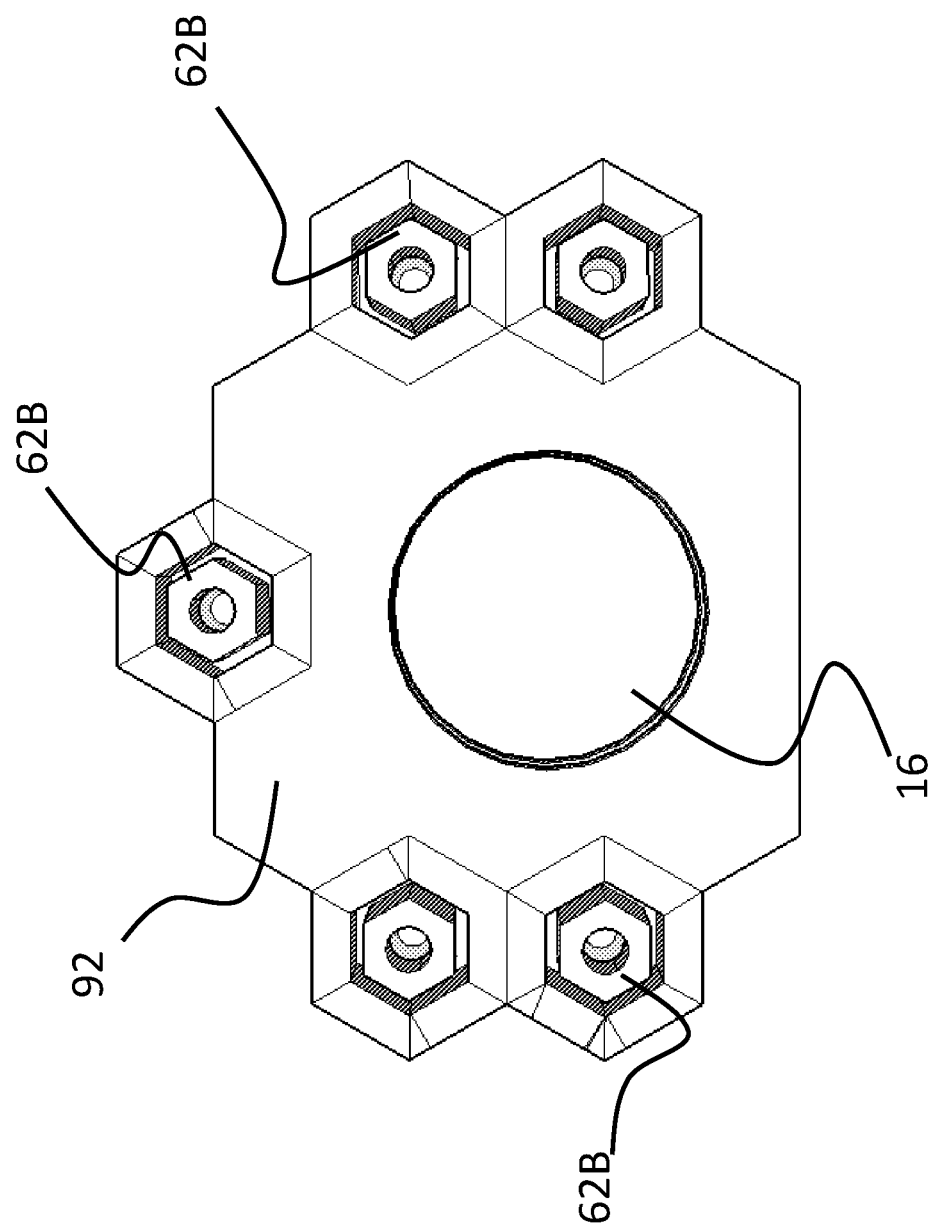
FIG. 13 is a top down view of a detachably coupleable cell arrangement which cooperates with the outer periphery as shown in FIG. 12.

Referring now to FIG. 13 there is illustrated an embodiment of a detachably coupleable cell module 92, the module in this embodiment comprises a resiliently deformable body defining a void 16. The module includes detachably coupleable cells 22' to connect with other cells in the array. In the example shown the module has a plurality of second portions 62B of detachably coupleable cells 22' distributed around the periphery of the body. It will be appreciated that the module can be formed with as many types of musculoskeletal components as required, to be assembled into the orthoses, to aid complex MSK pathologies. For example, the modules can come in multiple size pads, to aid customisation to each foot type; rear foot and forefoot medial and lateral wedging, heel raises, heel cups of multiple sizes, Morton's neuroma domes; metatarsal domes, and adequate cell removal to gain sagittal first plane functional 1st ray correction.

Figure 14:
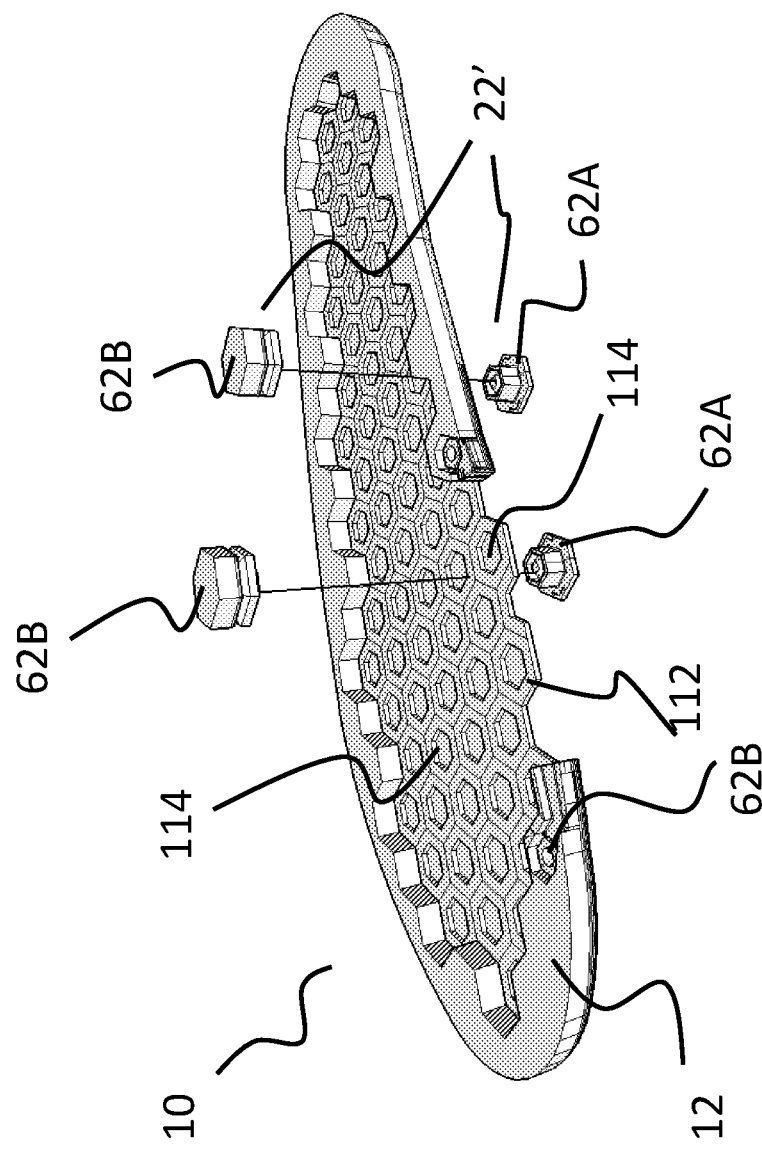
FIG. 14 is an exploded view of an orthotic device according to an embodiment of the present invention.

FIG. 14 shows a representation of an embodiment of the device 10 wherein the array of cells 22/22'/22" have been removed from a cell frame 110 and a modified segment 42' has been removed from the outer periphery 12. The detachably removable cells 22' shown comprise a first portion 62A separably joinable with a second portion 62B. The cells are joined by inserting the protuberance 66 of the first portion through the cell frame aperture 114 into the recess 68 of the second portion and are separated with a reverse action. The cell frame mesh 112 is shown connected to the outer periphery 12. The outer periphery 12 has had a modified segment 42' removed, forming a void 16. Disposed on the outer periphery 12 adjacent to the void are second portions of detachably coupleable cells second portions 62B, these can correspond with the removed segment or be joinable with first cell portions of a bridge to be added.

In an example of use of the orthotic device with additional features, a clinician would place the complete orthotic device 10 adjacent the underside of a patient's foot (not shown) and the translucent/transparent property of all cells 22', outer periphery 12 and frame 110 enables the clinician to associate the trauma locations on the patient's foot with the corresponding location on the device. The clinician then removes those cells 22' corresponding to the location of the trauma to create the voids 16 in the body 11 at these locations which require offloading. The cells may be removed one at a time from the cell frame by separating the first portion 62A from the second portion 62B simply by manipulating the resilient deformable device 10 and manually pulling apart the portions. Furthermore, where there are locations of trauma corresponding with the side of the foot, segments 42 of the outer periphery 12 may be removed in a similar manner to the cells 22'. The removed cells 22' or segments 42 may be replaced with modified segments 42' comprising bridges 82 or modules 92 which provide further musculoskeletal components, the modified segments 42' or modules having either or both cells portions which allow them to detachably coupled with other features of the device, such as through the cell frame 110 or to the outer periphery 112. The clinician can suitable modify the device by removing as many of the modular components and adding any additional components as necessary to suit the patient needs. The device is hygienic, the cells 22' and modified segments 42' are capable of being reattached to fill the voids 16, it is envisaged that this device 10 can be subsequently re-configured to correspond to on going treatment and recovery requirements, or reuse.

Figure 15:
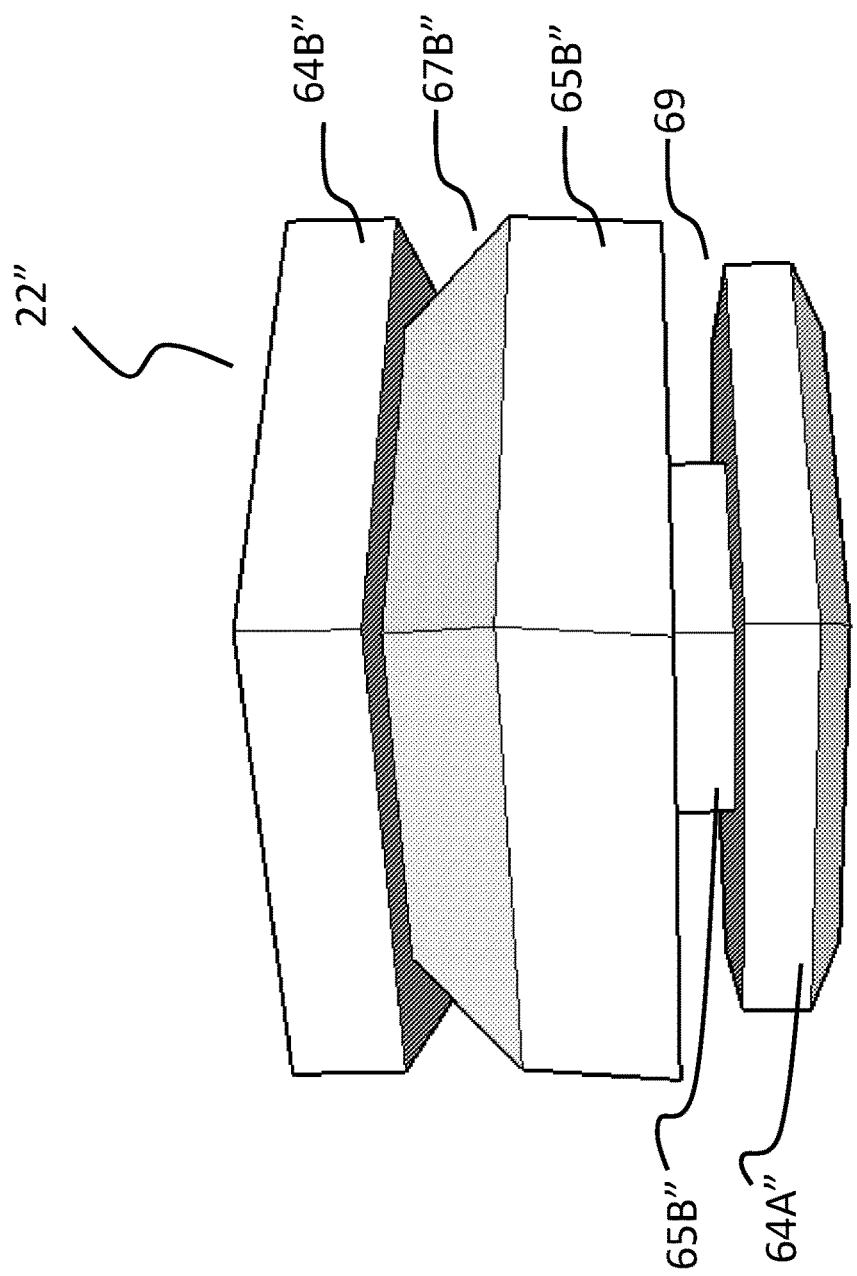
FIGS. 15, 16 and 17 are a series of views of a modified alternative embodiment of a detachably coupleable cell.

Referring now to FIG. 15 there is shown a modified alternative embodiment of a detachably coupleable cell 22', namely modified alternative cell 22" wherein the cell 22"

comprises a unified cell body. Unlike the embodiment in FIGS. 6A and 6B the equivalent first portion 62A and a second portion 62B create a single cell and are not detachably coupleable. FIG. 15 illustrates a side view of a cell 22" the unified body of the cell comprising at a surface opposing end, a base 64A" and a post 65A", and at a foot opposing end, a cap 64B" and a flange 65B". There is a groove 67B" formed between the cap and flange extending around the circumference of the cell, which as the cell is formed of a resiliently deformable material can allow compression under load, achieving a low pressure gradient around the periphery of an offload site (void). There is a channel 69 formed between the base 64A" and flange 65" extending around the circumference of the post 65A", this channel forms part of the coupling means for attaching the cell 22" to the cell frame mesh 112. In use one or more cells 22" are passed through an aperture 114 of the cell frame and the frame 110 is located in the channel 69.

In a preferable embodiment, the detachably coupleable cell 22" comprises a depth of approximately 6 mm; however it will be appreciated that the dimensions of the cells may be modified to suit individual circumstances. In the embodiment, the cells comprise a substantially hexagonal prism shape, however, further shapes may be envisaged such as octagonal or cuboid.

Figure 16:
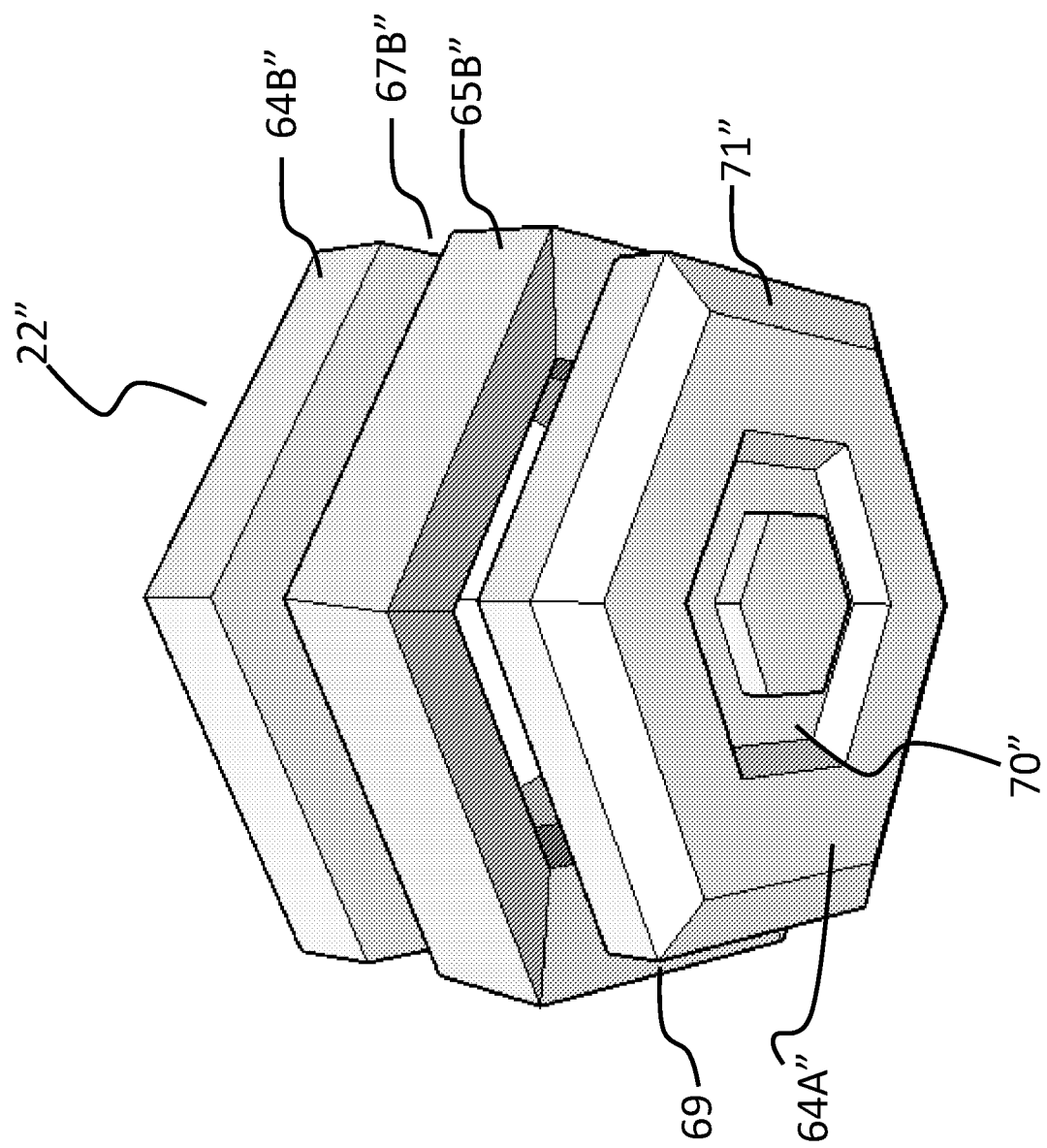

FIG. 16 illustrates an isometric view of the modified alternative cell 22" showing the unified body of the cell comprising at a surface opposing end, a base 64A" and a post 65A", and at a foot opposing end, a cap 64B" and a flange 65B", a groove 67B" formed between the cap and flange extending around the circumference of the cell, and, channel 69 formed between the base 64A" and flange 65" extending around the circumference of the post 65A". Further shown is indentation 70", in the embodiment shown the indentation is hexagonal, as the cell is formed of resiliently deformable material the indentation allows the base 64A" to deform as it is passed through the aperture 114 of a cell frame 112 and then return to its original shape, thus retaining the mesh 112 in channel 69. It will be appreciated that the indentation may take multiple forms such as a plurality of separate indentations on the base 64", to allow the goal of improving the deformation characteristics to be achieved. Further shown is that base 64A" is bevelled 71" around its circumference (shaped to direct the base through the aperture e.g. running outwards); this further improves the ability of the cell 22" to pass through the cell frame 110.

Figure 17:
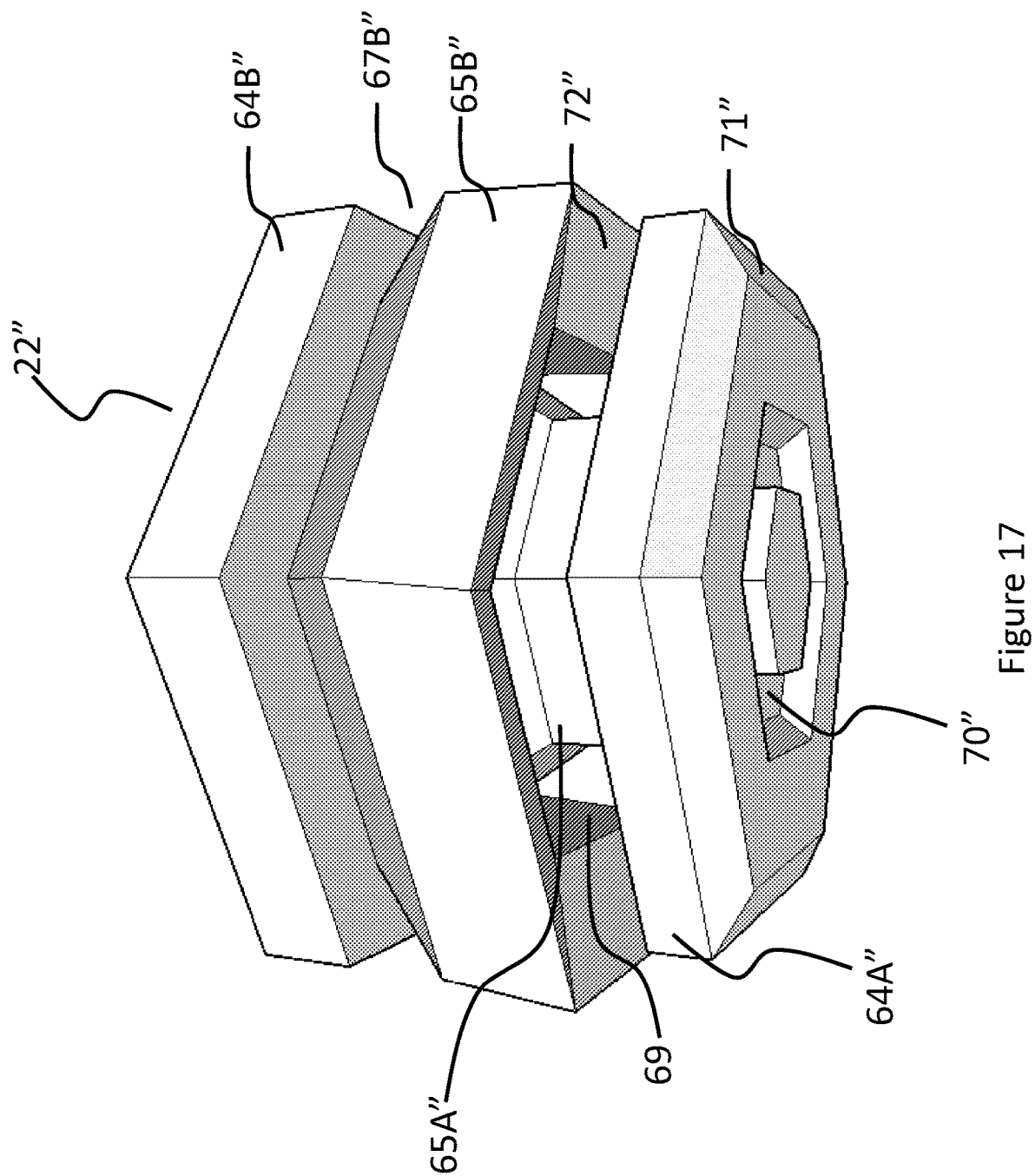

FIG. 17 illustrates an isometric view of the modified alternative cell 22" showing the unified body of the cell comprising at a surface opposing end, a base 64A" with indentation 70 and bevelling 71 and a post 65A", and at a foot opposing end, a cap 64B" and a flange 65B", a groove 67B" formed between the cap and flange extending around the circumference of the cell, and, channel 69 formed between the base 64A" and flange 65" extending around the circumference of the post 65A". Further shown is that flange 65B", is wider than base 64A" and is bevelled 72 around its circumference, (e.g. running inwards opposite direction to the bevel on 71 on base 64A"). In use when the base 64A" is passed through the cell frame 110, the flange 65B" may contact the mesh 112, where upon the flange will deform outwards and not pass through the aperture 114, the cell frame 110 will then be located in the channel 69 and cell 22" is coupled to the frame, only being uncoupleable by sufficient force and deformation, for example by a clinician removing the cell 22". It will be appreciated that the exact dimensions of the cell, included the individual features such as the base, flange and cap, can be varied in dependence on factors such as dimensions of the cell frame. For example, where a patient my require a greater degree of specific offloading then the size of the cell and corresponding features may be small and vice versa.

The cell 22" is a single component of the offloading orthotic device 10. The cell 22" can deform and return to its original form during the process of detaching and coupling the cell to the frame 110 of the orthotic. This can be applied to every similar cell in the orthotic, for example such as those used on a fragment 42' or module 92 to attach to the frame 110.

In an example of use of the orthotic device with the modified alternative embodiment of a detachably coupleable cell 22", a clinician would place the complete orthotic device 10 adjacent the underside of a patient's foot (not shown) and the translucent/transparent property of all cells 22", outer periphery 12 and cell frame 110 enables the clinician to associate the trauma locations on the patient's foot with the corresponding location on the device. The clinician then removes those cells 22" corresponding to the location of the trauma to create the voids 16 in the body 11 at these locations which require offloading. The cells 22" may be removed one at a time from the cell frame by manipulating the resilient deformable device 10, specifically the cells 22", such that the base 64A" deforms and passes through the apertures 114 of cell frame 110. Furthermore, where there are locations of trauma corresponding with the side of the foot, segments 42 of the outer periphery 12 may be removed in a similar manner to the cells e.g. deformation. The removed cells 22" or segments 42 may be replaced with modified segments 42' comprising bridges 82 or modules 92 which provide further musculoskeletal components, the modified segments 42' or modules having further cells 22" disposed upon them to detachably coupled with other features of the device, such as through the cell frame 110. The clinician can suitable modify the device by removing as many of the modular components and adding any additional components as necessary to suit the patient needs. The device is hygienic, the cells 22" and modified segments 42' are capable of being reattached to fill the voids 16, it is envisaged that this device 10 can be subsequently re-configured to correspond to on going treatment and recovery requirements, or reuse.

Select embodiments of the invention only have been described and illustrated, and it will be readily apparent that other embodiments, modifications, additions and omissions are possible within the scope of the invention.

The apparatus of the invention may be varied according to requirements, having as its ultimate objective to provide a fully customisable, adhesive free insole that can instantly offload any high-pressure areas of the foot simply by removing desired cells.

What is claimed is:

1. An orthotic device for a shoe, wherein the shoe comprises a longitudinal axis (Y) which extends between a front and a rear of the shoe, and a lateral axis (X) which extends between a left and a right side of the shoe, substantially transverse to the longitudinal axis, the device comprising:
    a substantially planar body having a resiliently deformable outer peripheral portion;
    a cell frame; and
    an inner array of detachably coupleable cells, wherein each cell comprises cell coupling means which permit the cells to detachably couple with the cell frame, characterised in that the outer peripheral portion comprises a plurality of peripheral segments each comprising coupling means, which permit the peripheral segments to detachably couple together.

2. An orthotic device according to claim 1, wherein the cell coupling means permit the cells to detachably couple with each other.

3. An orthotic device according to claim 1, wherein the cell coupling means permit the cells to detachably couple with an outer periphery.

4. An orthotic device according to claim 1, wherein the cells comprise a hexagonal prism.

5. An orthotic device according to claim 1, wherein the cells comprise a plurality of cell faces.

6. An orthotic device according to claim 5, wherein the cell coupling means comprise one or more protuberances and/or recesses located on the cells faces.

7. An orthotic device according to claim 6, wherein the one or more protuberances extend outwardly of each of the cells, away from the respective cell faces and the recesses extend inwardly of each of the cells, from each of the respective cell face.

8. An orthotic device according to claim 1, wherein the cells are orientated such that an interface between neighbouring cells extends non-parallel with the longitudinal axis (Y) and lateral axis (X) of the shoe.

9. An orthotic device according to claim 1, wherein the orthotic device is composed of silicone.

10. An orthotic device according to claim 1, wherein the cells are composed of a closed cell material.

11. An orthotic device according to claim 1, wherein the orthotic device is composed of a translucent or a transparent material.

12. An orthotic device according to claim 1, wherein the detachably coupleable cells each comprise a first cell portion and a second cell portion which are detachably coupleable.

13. An orthotic device according to claim 12, wherein the first cell portion and the second cell portion separately comprise a male or a female connector.

14. An orthotic device according to claim 1, wherein the cell frame comprises a resiliently deformable mesh defining a plurality of apertures.

15. An orthotic device according to claim 14, wherein each of the cells comprises a base and a cap, wherein each of the cell coupling means comprise a channel formed between the base and the cap.

16. An orthotic device according to claim 15, wherein the cell frame is located in the channel of each of the cells when each of the cells are coupled to the cell frame.

17. An orthotic device according to claim 1, further comprising one or more cell modules, wherein each cell module comprises a body and one or more of the detachably coupleable cells.

* * * * *